United States Patent [19]

Engeljehringer et al.

[11] Patent Number: 5,243,847
[45] Date of Patent: Sep. 14, 1993

[54] METHOD AND APPARATUS FOR THE INDIRECT IDENTIFICATION OF MASS FLOW

[75] Inventors: Kurt Engeljehringer, Graz; Harald Koch, Frauental; Wolfgang Schindler, Graz, all of Austria

[73] Assignee: AVL Gesellschaft fur Verbrennungskraft-maschinen und Messtechnik mbH., Austria

[21] Appl. No.: 728,153

[22] Filed: Jul. 10, 1991

[30] Foreign Application Priority Data

Jul. 11, 1990 [AT] Austria .................. 1478/90

[51] Int. Cl.$^5$ .............................. G01F 25/00
[52] U.S. Cl. ............................ 73/3; 73/195; 364/510
[58] Field of Search ............ 73/3, 195, 861.04, 861; 364/571.01–571.08, 510

[56] References Cited

U.S. PATENT DOCUMENTS 3,895,529  7/1975  Moore ..................... 364/510 X
4,341,107  7/1982  Blair et al. ..................... 73/3
4,671,097  6/1987  Kurki et al. ............... 364/510 X
4,823,591  4/1989  Lewis ........................... 73/3
5,038,608  8/1991  Sakai et al. ................. 73/3 X Primary Examiner—Tom Noland
Attorney, Agent, or Firm—Hill, Steadman & Simpson

[57] ABSTRACT

For the indirect identification of the mass flow of a specimen fluid stream, the specimen fluid stream is mixed with a dilution fluid stream to form an total fluid stream that is to be investigated in view of specific constituents of the specimen fluid stream. The mass flow of a specimen fluid stream is identified from the difference between the measured mass flows of the dilution fluid stream and the total fluid stream. In order to reduce the possibilities of error in the setting of a defined dilution ration, the mass flows of the dilution fluid stream and the total fluid stream are calibrated relative to one another, to which end one of the calibration measurements is not undertaken at the respective fluid stream but is separately undertaken at the specimen fluid stream.

10 Claims, 2 Drawing Sheets

METHOD AND APPARATUS FOR THE INDIRECT IDENTIFICATION OF MASS FLOW

BACKGROUND OF THE INVENTION

1. Field of the Invention:

The present invention relates to a method for the indirect identification of mass flow of a first fluid stream and to an apparatus for carrying out such method, whereby the first fluid stream is mixed with a second fluid stream and the mass flow of the first fluid stream is identified from the difference between the measured mass flows of the second fluid stream and of the mixed stream that has thereby arisen and whereby, for calibration, the mass flows of calibration streams are respectively measured and are employed for correction, as needed.

More particularly, the present relates to a method for the indirect identification of the mass flow of a specimen fluid stream that is mixed with, in particular, a significantly-greater dilution fluid stream to form an total fluid stream that is to be investigated in view of specific constituents of the specimen fluid stream, whereby the mass flow of the specimen fluid stream is identified from the difference between the measured mass flows of the dilution fluid stream and of the total fluid stream, and whereby the mass flows of calibration streams are respectively measured for calibration and are employed for correction, as needed.

Also more specifically, the invention is also directed to an arrangement for the investigation of a specimen fluid stream, comprising a specimen conduit for the specimen fluid stream discharging into a mixing volume, comprising a dilution conduit for a dilution stream likewise discharging into the mixing volume and comprising a mixed conduit for the total fluid stream that leads from the mixing volume to a suction device via an analysis unit, as well as comprising respective mass flow regulators in the dilution conduit and in the mixed conduit following the analysis unit that are connected to an evaluation unit for the indirect identification of the mass flow of the specimen fluid stream, and comprising a calibration arrangement for calibrating the mass flow regulators.

2. Description of the Prior Art:

A controlled mixing or, respectively, dilution of gaseous or liquid fluid streams is frequently required in the control and analysis of processes, as well as generally in measuring and control technology. To this end, flow regulators (for mass or volume streams) are known that offer defined, adjustable fluid streams. For gaseous fluid streams, for example, what are referred to as "thermic mass flow regulators" are known in this context as compact units and are commercially-available devices, these identifying the actual flow with a hot-wire anemometer and offering a certain reference flow on the basis of appropriate follow-up adjustment or readjustment devices. A defined specimen fluid stream $G_P$ can therefore have a generally significantly-different dilution fluid stream $G_V$ added thereto with such regulators, the dilution ratio q therefore resulting on the basis of the expression $$q = (G_V + G_P)/G_P.$$

The above inherently, extremely-simple known method can no longer be utilized when the specimen fluid stream is composed of, for example, aggressive substances that would chemically attack the regulators or of contaminated particleladen gases or liquids that continuously contaminate the regulators and mechanically destroy the same over a long term. Only one example in this respect is the dilution of diesel exhaust gas with air. Such a dilution is currently required by most jurisdictions before the measurement of contents of harmful substances, particularly of the particle content, in the exhaust gas in order to simulate emission conditions.

The above known method was developed for the indirect identification of the mass flow of the specimen fluid stream that is therewith necessary, the dilution fluid stream $G_V$ and the mixed stream or, respectively, total fluid stream $G_T$ thereby resulting being regulated therewith and the specimen fluid stream or, respectively, the dilution being calculated therefrom in accordance with the relationship $$G_P = G_{TOT} - G_V \text{ or, respectively,}$$
$$q = G_{TOT}/(G_{TOT} - G_V).$$

The identification or, respectively, follow-up readjustment of the mass flow is therefore limited, on the one hand, to the unloaded dilution fluid stream and, on the other hand, to the mixed stream or, respectively, total fluid stream (from which the loading by the specimen fluid stream can, in turn, already be filtered out at this location), this avoiding the above-described disadvantages.

This latter, so-called difference control method can be extremely-well utilized given relatively-low mixing or, respectively, dilution ratios (q<10). The throughput or, respectively, flow regulators for the total fluid stream $G_{tot}$ and for the dilution fluid stream $G_V$ must, in fact, generally be calibrated from time-to-time since, in particular, the measured value pick-ups of the regulating units are subject to chronological drifts and fluctuations; since, however, the accuracy and reproducibility of these units lies about or, respectively, below 1% based on the current technical standard, the specimen fluid stream $G_P$ can usually still be set with adequate accuracy for low dilution rates.

However, there is currently frequently the demand to also be able to set higher dilution ratios, whereby, however, it has been shown that extremely-great inaccuracies then occur in the setting of the specimen fluid stream $G_P$ and of the dilution ratio q, even when the flow regulators for the total fluid stream $G_{tot}$ and the dilution fluid stream $G_V$ are calibrated with the same units. This becomes clear on the basis of a simple numeric example. When, for example, the regulator for the total stream $G_{TOT}$ and for the dilution fluid stream $G_V$ is calibrated 0.5% too low and the regulator for the dilution fluid stream $G_V$ is calibrated 0.5% too high, then, given the setting of a dilution ratio of q=20, one obtains an actual dilution ratio of q'=24.72 in accordance with the above equation, i.e. an error of 23.6%.

In order to suppress this systematic error, a feature of the difference regulating method has been disclosed in accordance wherewith small sub-streams are branched off from the specimen fluid stream and from the total fluid stream, the concentration of a characteristic constituent then being measured at the sub-streams and being employed for the readjustment of the flow regulator for the dilution fluid stream $G_V$ and/or the total fluid stream $G_{TOT}$. For the above-addressed example of the dilution of diesel exhaust gas, for example, the measurement of exhaust gas constituents $CO_2$ or $NO_X$ is available. This feature, however, requires a significantly-greater expense that, in the view of costs and apparatus equipment, frequently amounts to a multiple of that for the actual mixing or, respectively, dilution device itself.

SUMMARY OF THE INVENTION

It is an object of the present invention to provide an improved method, based upon the known method set forth above and, respectively, an improved apparatus based on the arrangement addressed above such that the disadvantages of the known method and known apparatus and features thereof are avoided and such that, in particular, a more accurate setting of even high dilution ratios becomes possible in a simple manner.

In the method of the species initially set forth, this is achieved in that the mass flows of the second fluid stream or, respectively, of the dilution fluid stream and of the mixed stream or, respectively, of the total fluid stream are calibrated relative to one another, to which end one of the calibration measurements is separately undertaken at the first fluid stream or, respectively, the specimen fluid stream.

Accordingly, the calibration arrangement, given the initially-addressed arrangement, comprises a measuring unit which may be introduced into the specimen conduit for calibration for identifying the mass flow of the specimen fluid stream that is preferably connected to an input of a comparator unit that has a further input also connected to the evaluation unit.

The mass flow regulators for the total fluid stream $G_{TOT}$ and the dilution fluid stream $G_V$ are therefore no longer calibrated absolutely and independently of one another. This standard type of calibration having a known, separately-supplied calibration stream is undertaken only at one of the flow quantity regulators (for calibrating the respective other flow quantity regulator) and a calibrating measurement is undertaken directly at the first fluid stream or, respectively, the specimen fluid stream and the assigned mass flow regulator is adjusted on the basis of this calibrating measurement such that the correct mixing or, respectively, dilution ratio $q = G_{TOT}/G_P$ results. An error of 0.5% in the calculation of the mixed stream or, respectively, total fluid stream $G_{TOT}$ therefore now only effects an error of 0.5% in the dilution ration q, as a result whereof the total error of the ratio q lies below 1.5%, since the first fluid stream or, respectively, the specimen fluid stream $G_P$ can likewise be defined with an accuracy of approximately 1% (as a result of the lower values, the relative measuring error for the specimen fluid stream $G_P$ is generally greater than for the total fluid stream $G_{TOT}$ and the dilution fluid stream $G_V$).

The measuring unit for calculating the mass flow that can be introduced into the specimen conduit or, respectively, into the conduit for the first fluid stream, in accordance with the present invention, for calibration can, for example, can be carried out by a dry gas meter, by what is referred to as a laminar flow element or with similar, simple devices, whereby, of course, the composition of the first or, respectively, the specimen fluid stream must be taken into consideration on a case-by-case basis. Since, on the one hand, the requirement of influencing the mass flow at this location is eliminated and, on the other hand, calibration measurements are usually only briefly punctually implemented, difficulties of the type initially set forth need not be feared by these measurements.

According to an advantageous embodiment of the method of the invention, the calibrating measurement at the first fluid stream or, respectively, at the specimen fluid stream is employed, as needed, for correcting the respective mass flow (i.e., for correcting the mass flow here of that flow stream that is to be calibrated relative to the other fluid stream calibrated in the usual manner), particularly for correcting the mass flow of the dilution fluid stream. The aforementioned, particularly preferred embodiment is advantageous in many instances because the total fluid stream can therefore be kept constant, this, for example, enabling densitometry or, respectively, measurements of the particle loading at the diluted diesel exhaust gas given constant flow rate. The corresponding embodiment of the arrangement of the present invention is characterized in that an output of a comparator unit is connected to an adjustment input of the mass flow regulator for the dilution fluid stream.

In accordance with another, preferred embodiment of the invention, however, it can also be provided that the calibration measurement at the first fluid stream or, respectively, at the specimen fluid stream is employed, as needed, for correcting the result of the formation of the difference. In this arrangement constructed in accordance with the present invention, is provided in this context that one output of the comparator unit is in communication with a correction with the result of the evaluation unit. In accordance with the foregoing, one of the two, unloaded fluid streams thereby continues to be calibrated in a standard manner with the calibration stream. The other, unloaded fluid stream or, respectively, the appertaining flow regulator is now only indirectly calibrated in that the measured or, respectively, evaluation result of the first or, respectively, the speciment fluid stream is corrected such that the calibration measurement of the flow of the loaded first or, respectively, the loaded speciment fluid stream that the amount of the fluid stream that is not directly calibrated is properly evaluated.

This latter embodiment of the invention is particularly advantageous in conjunction with another improved feature of the invention in accordance wherewith the dilution fluid stream is set to a fixed succession of different mass flows, the appertaining calibration measured values for the mass flow of the specimen fluid stream are required, an assignment between the mass flows that are set and the appertaining measured values is undertaken and the mass flow of the specimen fluid stream is calculated therefrom and displayed for each set value of mass flow of the dilution fluid stream. This feature of the invention proves advantageous, particularly given the utilization of automatic measured data acquisition and evaluation systems in which, in accordance with a further feature of the invention, the setting, assignment and calculation can occur at least partially automatically, preferably under the control of a computer as well. A defined sequence of settings of the respective reference value generator can therefore be implemented during a calibration cycle and an acquisition and storing of the appertaining measured values can be simultaneously undertaken. On the basis of suitable calculating operations, the appertaining specimen fluid stream can be directly calculated during operation of the total measuring arrangement for each arbitrary setting of, for example, the reference value generator or the mass flow of the dilution fluid stream and the dilution ratio can be calculated therefrom.

These latter features of the method of the invention, of course, can also be advantageously employed in conjunction with the more general method addressed above (with the mixing of the first and second fluid streams to form a mixed stream).

BRIEF DESCRIPTION OF THE DRAWING

Other objects, features and advantages of the invention, its organization, construction and operation will be best understood from the following detailed description, taken in conjunction with the accompanying drawing, on which.

DESCRIPTION OF THE PREFERRED EMBODIMENTS

Figure 1:
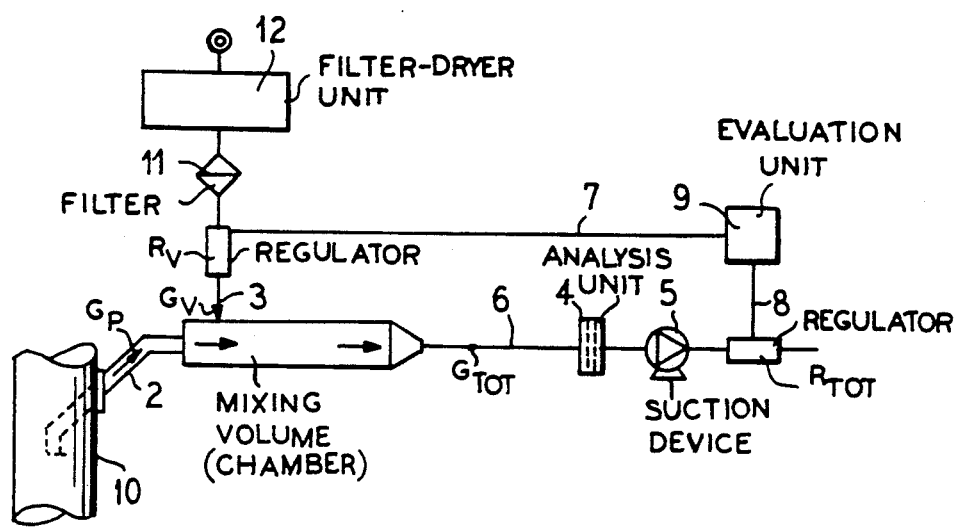
FIG. 1 is a schematic circuit diagram of an arrangement constructed in accordance with the present invention for the investigation of a specimen fluid stream.

The arrangement for the investigation of a specimen fluid stream $G_P$ schematically illustrated in FIG. 1 as comprising a specimen conduit 2 for the specimen fluid stream $G_P$, the conduit 2 discharging into a mixing volume or container 1, a dilution conduit 3 for a dilution fluid stream $G_V$ that likewise discharges into the mixing volume 1 and also comprises a mixed conduit 6 for the total fluid stream $G_{TOT}$ that leads from the mixing volume 1 via an analysis unit 4 to a suction device 5. A mass flow regulator $R_V$ is introduced into the dilution conduit 3 and a mass flow regulator $R_{TOT}$ is introduced into the mixed conduit 6 following the analysis unit 4 and the suction device 5, these regulators being connected by way of respective lines 7 and 8 to an evaluation unit 9 for the indirect evaluation of the mass flow of the specimen fluid stream $G_P$. In addition, the regulators $R_V$ and $R_{TOT}$ are also in communication (in a manner not illustrated here) with a calibration arrangement whose operation in accordance with the invention shall be set forth below with respect to FIGS. 3 and 4. For the sake of completeness, an exhaust gas pipe 10 should also be pointed out with respect to FIG. 1, the specimen fluid stream $G_P$ being branched off therefrom for dilution and analysis. A filter 11 and a filter-dryer unit 12 are also indicated in the dilution conduit 3.

Insofar as can be seen from FIG. 1, the arrangement of the present invention or, respectively, the method implemented therewith, does not differ from that of the prior art. The critical difference lies in the type of calibration (not shown in FIG. 1) of the mass flow regulators $R_V$ and $R_{TOT}$ or, respectively, in the different arrangement parts and linkages required for this purpose, as shown with respect to the prior art in FIG. 2, on the one hand, and with respect to the present invention in FIGS. 3 and 4, on the other hand.

Figure 2:
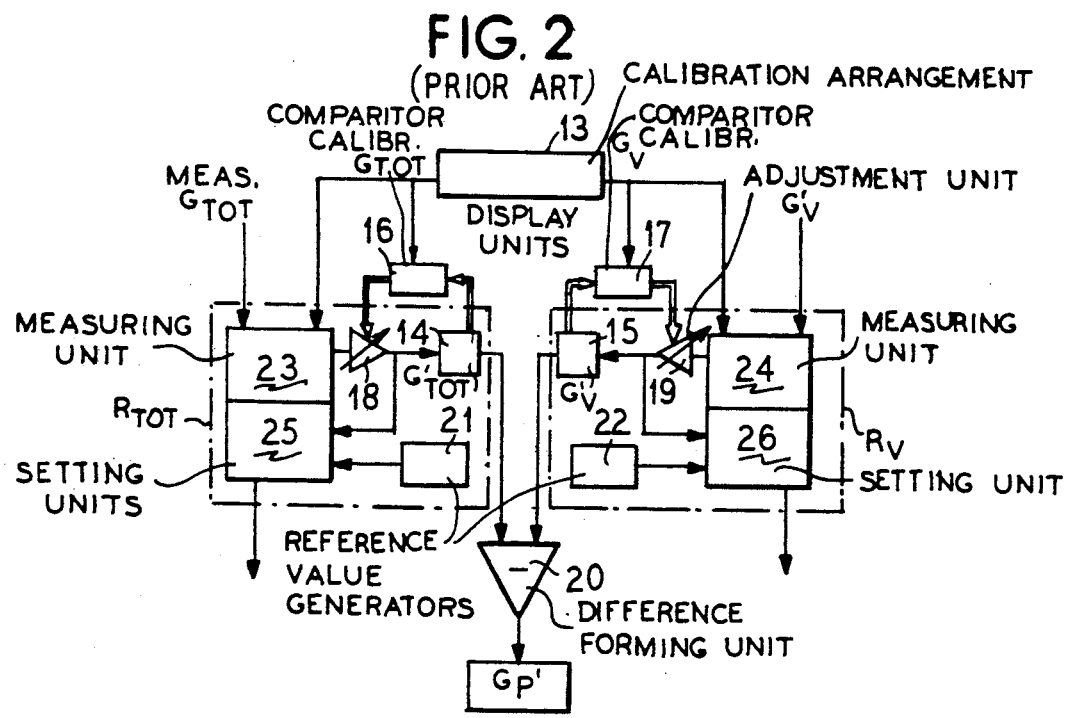
FIG. 2 is a schematic circuit diagram directed to the prior art in conjunction with the calibration of the arrangement of FIG. 1.

According to FIG. 2, the internal structure of the mass flow regulators $R_V$ and $R_{TOT}$, as well as the internal and external interactions in the calibration of these regulators are shown by way of example for typical units of this type. For calibration, the regulators $R_{TOT}$ and $R_V$ are each respectively charged via the calibration arrangement 13 with the fluid stream $G_{TOT}^{CALIBR}$ or, respectively, $G_V^{CALIBR}$ that is known with respect to the mass flow. Given a deviation of the display $G_{TOT}'$ or, respectively, $G_V'$ at the display units 14, 15 (identified via the comparators 16 and 17), an adjustment unit 18 or 19, respectively, is adjusted until the display value corresponds to the calibration value. The adjustment unit 18, 19 can thereby operate electronically in an analog manner or, respectively, electronically in a digital manner, pneumatically, mechanically or thermally and, for example, can be composed of an electronically-variable amplifier circuit and of a linearization circuit. This setting or, respectively, adjustment is indicated by the arrows through the adjustment units 18 and 19 and by the double-line arrows between the units 14, 16, 18 or, respectively, 15, 17, 19 and can occur both automatically and by way of the operating personnel. After the calibration, the specimen fluid stream $G_P$ is calculated during normal operation of the arrangement by forming the difference between the total fluid stream $G_{TOT}$ and the dilution fluid stream $G_V$ and the dilution ratio q is calculated by division of the value of $G_{TOT}$ by the value $G_P$.

The unit for forming the difference is referenced 20 in FIG. 2. Reference value generators 21 and 22 are provided for the mass flow regulators $R_{TOT}$ and $R_V$, respectively. The measuring units of the regulators $R_{TOT}$ and $R_V$ are indicated at 23 and 24, respectively, and the setting units are illustrated at 25 and 26, respectively.

Figure 3:
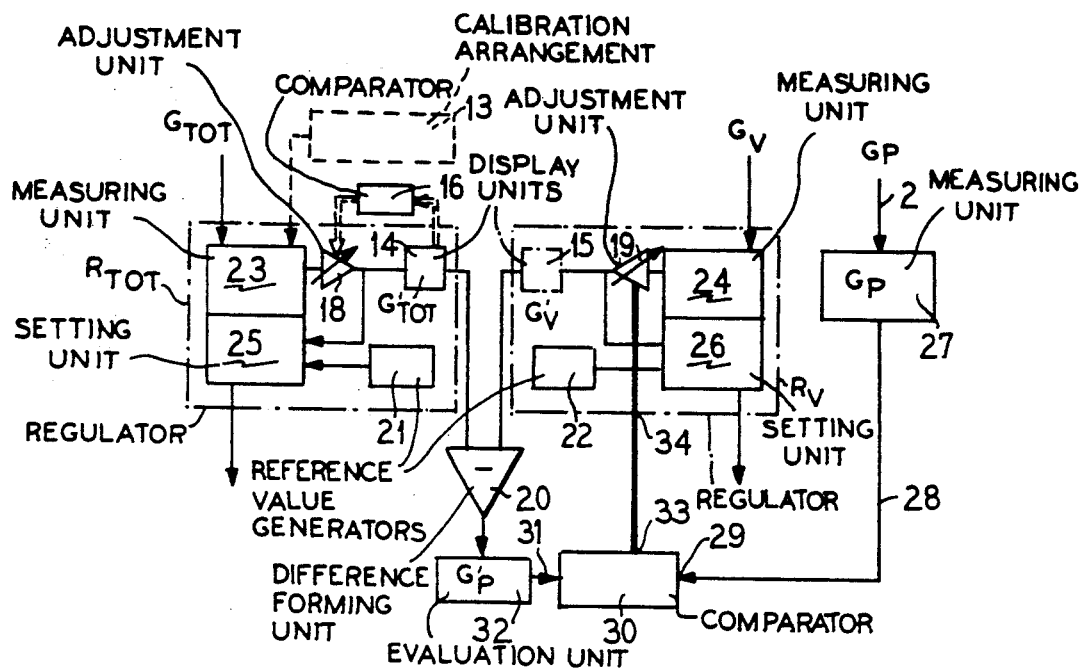
FIG. 3 is a schematic circuit diagram corresponding to that of FIG. 2 for the method or, respectively, for the arrangement of the present invention.
Figure 4:
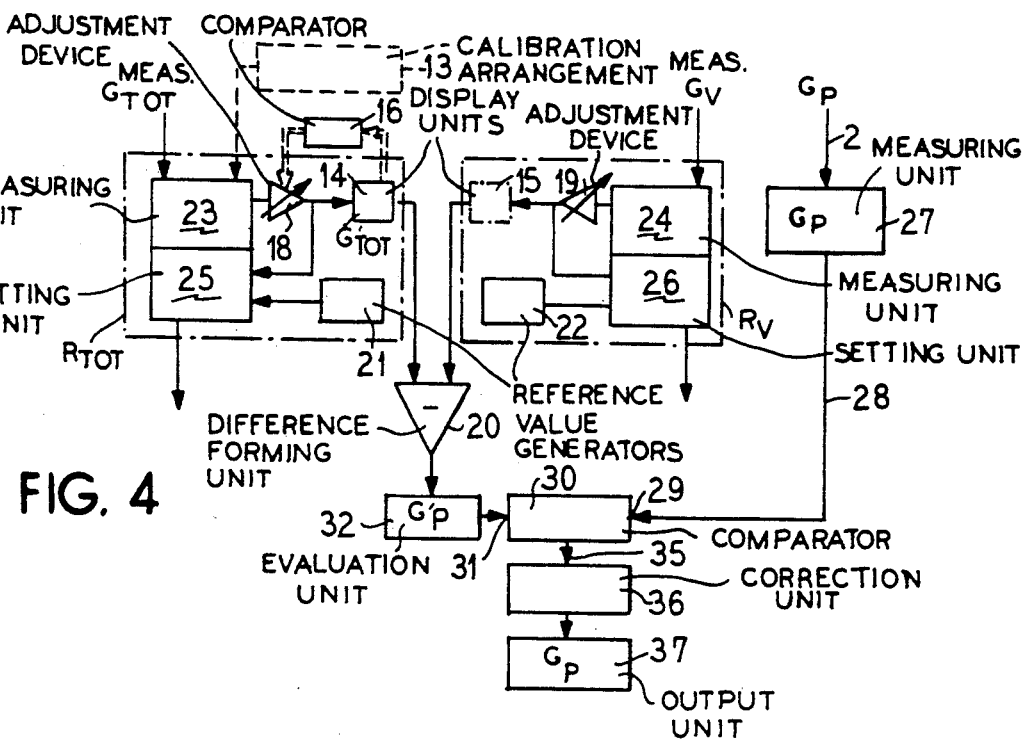
FIG. 4 illustrates a further circuit diagram of the same type showing another embodiment of the invention.

Given the absolute, mutually-independent calibration of the regulator $R_{TOT}$ and the regulator $R_V$ implemented in accordance with FIG. 2, the aforementioned and described errors in the dilution ratio actually set occur as a result of the relationships initially set forth and these errors, as mentioned above, can have serious effects, particularly given high dilution ratios. According to FIGS. 3 and 4 which, as mentioned, document various examples of the development of the invention, the mass flow regulators $R_{TOT}$ and, respectively, the internal and external executions at these mass flow regulators, given calibration, are again schematically illustrated at the left side, whereby the structure and the execution of the method do not significantly differ from the arrangement of FIG. 2. What is different in the structures of FIGS. 3 and 4 is the right-hand region assigned to the mass flow regulator $R_V$ or, respectively, to the calibration directed thereto. In both instances, the calibration arrangement 13 has a measuring unit 27 inserted into the specimen conduit 2 for identifying the mass flow of the specimen fluid stream $G_P$ assigned thereto, this being connected via a line 28 to an input 29 of a comparator 30 that a further input 31 in communication with the evaluation unit 32.

In the embodiment of FIG. 3, an output 33 of the comparator 30 is connected to an adjustment input 34 of the mass flow regulator $R_V$ and, in turn, acts on the adjustment unit 19 thereat, so that a deviation of the actual specimen fluid stream $G_P$ appearing in the calibration of the specimen fluid stream $G_P$, identified at the evaluation unit 32 leads to a corresponding readjustment of the mass flow regulator $R_V$ (and, in particular, relative to the calibration of the regulator $R_{TOT}$). According to FIG. 4, one output of the comparator unit 30 is in communication with a correction unit 36 for the result of the evaluation unit 32 that itself, in turn, lies at an output unit 37 which indicates the correspondingly-corrected value for the specimen fluid stream $G_P$.

Both according to FIG. 3 and FIG. 4, the regulator $R_{TOT}$ can either be realized, in shown, by an adjustable and calibratable control device or, on the other hand, by a unit that, on the basis of its type, sets the fluid stream $G_{TOT}$ to one or more constant values. For this reason, the calibration arrangement 13 and the double-line arrows for the potentially-necessary readjustment are only illustrated with broken lines. As one of many possible examples, a pressure regulator in combination with a flow resistance device may be considered. The only thing that is thereby critical is that the fluid stream $G_{TOT}$ is known with the same accuracy and is constant with at least the same accuracy over the desired operating time interval as required of the dilution ratio q. The mass flow regulator $R_V$ must continue to be adjustable; however, as mentioned, it is not absolutely calibrated, but respective relative to the value of the total fluid flow $G_{TOT}$. This calibration must occur for a number of values of the fluid flow $G_P$ when different dilution ratios q must be set during the operating time interval.

With reference to an example, it was shown above that, given a ratio q=20, an inaccuracy of ±0.5% in the adjustment can lead to a relative error of more than 20% given the known method (with the calibration according to FIG. 2). In the method practice in accordance with the present invention comprising the calibration according to FIGS. 3 or 4, significantly lower maximum errors result since a relative adjustment error of ±0.5% in the specimen stream flow $G_P$ (which, for example, can arise due to measuring inaccuracy of the specimen fluid flow $G_P$ can only act on all dilution ratios q with a relative error of ±0.5%.

Although we have described our invention by reference to particular illustrative embodiments thereof, many changes and modifications of the invention may become apparent to those skilled in the art without departing from the spirit and scope of the invention. We therefore intend to include within the patent warranted hereon all such changes and modifications as may reasonably and properly be included within the scope of our contribution to the art.

We claim:

1. In a method for the indirect identification of the mass flow of a first fluid stream by mixing the first fluid stream with a second fluid stream and calculating the mass flow of the first fluid stream from the difference between the measured mass flows of the second fluid stream and of a resulting mixed fluid stream, and in which mass flows of calibrating streams are measured for calibration and applied for correction, the improvement comprising the steps of:

calibrating the mass flows of the second fluid stream and of the mixed fluid stream relative to one another including performing a calibration measurement separately at the first fluid stream.

2. The improved method of claim 1, and further comprising the step of:

correcting a respective one of the mass flows with the calibration measurement of the first fluid stream.

3. The improved method of claim 1, and further comprising the step of:

correcting the result of the difference formation between the measured mass flows with the calibration measurement of the first fluid stream.

4. In a method for the indirect identification of the mass flow of a specimen fluid stream by mixing the first fluid stream with a significantly greater dilution fluid stream to form a total fluid stream that is to be investigated in view of defined component portions of the specimen fluid stream and including forming the difference between the measured mass flows of the dilution fluid stream and the total fluid stream to identify the mass flow of the specimen fluid stream, and including measuring mass flows of calibrating streams for use for calibration as needed, the improvement comprising the steps of:

calibrating the mass flows of the dilution fluid stream and of the total fluid stream relative to one another by separately measuring a calibration result at the specimen fluid stream.

5. The improved method of claim 4, and further comprising the step of:

correcting the mass flow of the dilution fluid stream by applying the calibration measurement of the specimen fluid stream.

6. The improved method of claim 4, and further comprising the step of:

correcting the result of the formation of differences between the mass flows of the dilution fluid stream and the total fluid stream with the calibration measurement of the specimen fluid stream.

7. In a method for the indirect identification of the mass flow of a specimen fluid stream by mixing the first fluid stream with a significantly greater dilution fluid stream to form a total fluid stream that is to be investigated in view of defined component portions of the specimen fluid stream and including forming the difference between the measured mass flows of the dilution fluid streams and the total fluid stream to identify the mass flow of the specimen fluid stream, and including measuring mass flows of calibrating streams for use for calibration as needed, the improvement comprising the steps of:

calibrating the mass flows of the dilution fluid stream and of the total fluid stream relative to one another by separately measuring a calibration result at the specimen fluid stream;

correcting the result of the formation of differences between the mass flows of the dilution fluid stream and the total fluid stream with the calibration measurement of the specimen fluid stream;

setting the dilution fluid stream to a fixed sequence of different mass flows;

assigning calibration measured values for the mass flow of the specimen fluid stream to the fixed different mass flows;

assigning the set mass flows and appertaining measured values;

calculating the mass flow of the specimen fluid stream therefrom for each set value of mass flow of the dilution fluid stream; and displaying the calculated value of the specimen fluid stream.

8. The improved method of claim 7, and further defined by:

automatically performing the steps of setting, assigning and calculating, under computer control.

9. In an arrangement for the investigation of a specimen fluid stream, and of the type comprising a specimen conduit for the specimen fluid stream discharging into a mixing container, in which a dilution conduit supports a flow of a dilution fluid stream into the mixing container, and in which a mixed conduit for the total fluid stream extends from the mixing container to a suction device via an analysis unit, and in which respective mass flow regulators are provided with a mass flow regulator in the dilution conduit and a mass flow regulator in the mixed conduit following the analysis unit, in which the regulators are connected to an evaluation unit for the indirect identification of the mass flow of the specimen fluid stream, and in which a calibration arrangement is connected to the regulators for calibrating the mass flow regulators, the improvement therein comprising:

- a measuring unit in the calibration arrangement and located in the specimen conduit for identifying the mass flow of the specimen fluid stream;
- a comparator connected to said measuring unit;
- an evaluation unit connected to said comparator;
- an adjustment unit in said regulator for said dilution fluid stream which is responsive to the output of said comparator to provide an adjustment of said mass flow regulator for said dilution fluid stream; and
- means connected to said mass flow regulators for forming the difference between the mass flows of the total fluid stream and the dilution fluid stream, said means connected to said evaluation unit as a controlling influence for said comparator.

10. In an arrangement for the investigation of a specimen fluid stream, and of the type comprising a specimen conduit for the specimen fluid stream discharging into a mixing container, in which a dilution conduit supports a flow of a dilution fluid stream into the mixing container, in which a mixed conduit for the total fluid stream extends from the mixing container to a suction device via an analysis unit, in which respective mass flow regulators are provided with a mass flow regulator in the dilution conduit and a mass flow regulator in the mixed conduit following the analysis unit, in which the regulators are connected to an evaluation unit for the indirect identification of the mass flow of the specimen fluid stream, and in which a calibration arrangement is provided for calibrating the mass flow regulators, the improvement therein comprising:

- a measuring unit in the calibration arrangement and located in the specimen conduit for identifying the mass flow of the specimen fluid stream;
- a comparator connected to said measuring unit;
- an evaluation unit connected to said comparator;
- a correction unit connected to said comparator for correcting the result of the evaluation unit; and
- a device connected to said correction unit for displaying a value of mass flow of the specimen fluid stream.

* * * * *